United States Patent [19]
Fritz

[11] Patent Number: 5,137,692
[45] Date of Patent: Aug. 11, 1992

[54] NITROGEN TEST KIT FOR PHYSICAL TRAINING

[76] Inventor: Robert Fritz, P. O. Box 1948, Martinez, Calif. 94553

[21] Appl. No.: 625,866

[22] Filed: Dec. 11, 1990

[51] Int. Cl.$^5$ .................. G01N 31/04; G01N 33/16; G01N 21/06
[52] U.S. Cl. .................. 422/61; 422/56; 422/57; 422/58; 422/82.05; 436/108; 436/113; 436/128; 424/7.1; 435/12
[58] Field of Search .................. 422/55-58, 422/61, 68.1, 82.05; 436/106, 107, 108, 111, 112, 113, 128, 165, 808; 424/7.1; 435/10, 12, 39

[56] References Cited

U.S. PATENT DOCUMENTS 3,531,254  9/1970  Okuda .................. 23/253

OTHER PUBLICATIONS

Orenerid, T. P., "A Rapid Bedside Method for Measuring Blood Urea," Practitioner 201:921.23 (1968).
Bold, AM et al, "An Assessment of the Azostix Strip Test," J. Clin. Path., 23:85-89 (1970).
Eckfeolt, J et al, "Urinary Urea: Are Currently Available Methods Adequate for Revival of an Almost Abandoned Test?" Clinical Chemistry, vol. 28, No. 7 pp. 1500-1502 (1982).
Skogerboe, K. J. et al, "Chemiluminescent Measurement of Total Urinary Nitrogen for Accurate Calculation of Nitrogen Balance", Clinical Chemistry, vol. 35, No. 5 pp. 752-755 (1990).
R. Fritz, Untitled, Reprint Journal of Sportscience, pp. 2-7 (1986).
(Brochure) "Semi-Quantitative Test for Urea Nitrogen in Whole Blood," (date unknown).

*Primary Examiner*—James C. Housel
*Assistant Examiner*—David Redding
*Attorney, Agent, or Firm*—Bielen, Peterson & Lampe

[57] ABSTRACT

A nitrogen test kit for determining the relative level of nitrogen of a user who is involved in a health program where diet and exercise are monitored and adjusted for optimizing physical development, the kit including a plastic stick having a reagent zone on which is included a reactant such as urease, and a pH indicator such as bromthymol blue, used in conjunction with color chart blocks representing a range of urea nitrogen concentrations, wherein the user's urine nitrogen content can be determined by comparing the altered color of the reagent zone of an exposed test strip to the color chart and compared with a personal baseline level, developed from a number of tests under controlled conditions, for determining the present protein nitrogen turnover and approximate balance.

5 Claims, 1 Drawing Sheet

NITROGEN TEST KIT FOR PHYSICAL TRAINING

BACKGROUND OF THE INVENTION

This invention relates to a non-invasive field kit to permit self-determination the relative level of a chemical agent in the urine of a person, particularly a person involved in a health program. In particular, the invention relates to a means to self-test urine using a disposable, indicator test strip having an impregnated reagent area for estimating the amount of urea nitrogen in the urine for determination of the nitrogen balance of a person in a dietary and physical exercise program.

It has been recently recognized that the rate at which an individual absorbs and excretes nitrogen is a good indicator of the individual's nutritional health. Particularly when an individual is involved in a program requiring both dietary control and physical activity, the nitrogen "balance" is considered to be critical in determining whether the individual will have a net physiological gain or loss from a particular physical session.

Nitrogen balance is a term used to define whether an individual is experiencing a net gain or loss in nitrogen, in the form of protein, as a result of his food intake and activity level. Useable nitrogen is added to the body through consumption of protein. Nitrogen is eliminated from the body through various pathways such as urine, feces, perspiration, menstruation and respiration. Other particular situational phenomena can add to normal losses, such as calorie reduction, injury, stress, heavy physical training, profuse sweating and abnormally low quality or quantity of protein intake. As heavy physical training is one known method of substantially altering the body's requirement for nitrogen in the form of dietary amino acids, it is desirable that anyone involved in strenuous athletic activity or in physical training, be conscious of his metabolic rate, and be particularly conscious of the assimilation, utilization and elimination of nitrogen compounds.

Unlike plants which can assimilate nitrogen from fertilizers and in certain cases directly from the air itself, a human is totally dependent upon protein for the daily requirements of nitrogen. The various amino acids that form the intake proteins are utilized for the resulting synthesis of body proteins. Synthesized proteins find their way into the formation of virtually all of the body's tissues, including most prominently muscle tissue, but also in hair, organs and to one degree or another almost in every other particle of the human body. When there is an equilibrium nitrogen balance, the proteins taken in by an appropriate diet replace those proteins that are metabolized or discarded on a daily basis. Dietary protein, therefore, s a critical factor in maintaining a nitrogen balance. Utilization of body protein during the process of athletic training, particularly strenuous activities such as weight training, can also affect the protein balance. Exercise leads to enhanced metabolization of both protein and available carbohydrates.

Clinical methods of determining the urea content and hence nitrogen content of whole blood and plasma have been developed. Furthermore, a reagent strip test method for estimating urea content of whole blood simplifies the test procedure and provides a useful screening test for uremia. The reagent strip test, however, requires at least one or two drops of blood and is therefore an inconvenient method for regular and repetitive testing, particularly for self-testing under less than antiseptic conditions.

Reagent strips such as pH indicators are a known means of providing a convenient method to approximate the acidity or alkalinity of a solution. The urea content of bodily fluids can be detected by reacting the urea with urease which catalyzes the hydrolysis of urea to carbon dioxide and ammonium hydroxide. The ammonium hydroxide quantitatively increases the pH of the solution and this increased pH is measured by color change of a pH sensitive indicator, such as bromthymol blue.

Although past invasive systems are inappropriate for the purposes proposed, this invention devises a means for adapting and utilizing the reagent strip screening test for monitoring nitrogen turnover and approximate balance, enabling a user to adjust his diet and exercise program according to quantitative results of convenient, self-administered urine tests. The urine tests are compared to a personal baseline developed by following a test regimen whereby the user is able to determine whether he or she is in a state of protein surplus or deficiency.

SUMMARY OF THE INVENTION

This invention relates to a system for determining the nitrogen turnover and status of a user who is involved in a health program where diet, exercise or both are monitored and adjusted for optimizing physical development. Since urea is predominantly discharged from the body through urine, testing the urea content of urine provides a non-invasive manner of determining the relative level of urea nitrogen in the system. Fluctuations in the urea content under controlled conditions can provide a quantitative method of determining the effect of emphasized factors in diet and training. By use of a simple quantitative test indicator, a training athlete or dieter can tailor his dietary and exercise program to maximize the body's protein utilization and minimize those situations where excess training or dieting may be deleterious to bodily development. The non-invasive indicator system of this invention comprises a kit including a plastic stick having a reagent zone on which is included a reactant such as urease, and a pH indicator such as bromthymol blue. By the use of color chart blocks representing a range of urea nitrogen concentrations, the user's urine nitrogen content can be personally determined by comparing the altered color of the reagent zone of an exposed test strip to the color chart. The indicator system can be adapted to include additional reagent zones for determining other nutritional status, such as vitamin, hormone or metabolite states, by appropriate reactants and color indicator means.

Although, a single sampling for nitrogen level will not provide sufficient basis for determining the nitrogen balance of the tested user, repetitive sampling under controlled conditions can establish a general personal level from which deviations can be detected that are indicative of changes in diet or training variables such as intensity, frequency and duration. As the test method is non-invasive, and can be accomplished in a simple procedure during normal urination with a discardable implement, repetitive sampling is a minimal burden. The system, while primarily used for human use is adaptable for use with animals, particularly those involved in strenuous training programs such as race horses, greyhounds and sled dogs.

Clinical methods of determining nitrogen balance require complex and exact determination of nitrogen intake and nitrogen discharge. Nitrogen intake is almost exclusively a factor of dietary intake of useable protein. Nitrogen loss is primarily in the form of eliminated urea. Urea is measured in excreted urine, feces and perspiration. Other nitrogen losses, such protein discard as hair loss during shaving, blood loss during menstruation and other nitrogen losses must be carefully measured. The nitrogen balance is determined by comparing the nitrogen intake with the nitrogen loss over a defined period of time. In a similar manner, the relative nitrogen balance can be determined by detecting the level of nitrogen excreted in the urine. While the level of nitrogen loss for various pathways may vary according to individuals, the quantitative measurement of the nitrogen level in the urine can provide an approximate indicator as to the current state of the individual when compared with a personal baseline developed by controlled measurements over a period of time. Urea content of the urine measured during relatively nascent periods of exercise with normal dietary habits can establish a preliminary baseline. Variations in exercise and diet, including dietary supplements, can assist in establishing a reliable personal baseline. Once the baseline is determined, deviations from the baseline as a result of defined activities can be detected to determine whether the individual is in a positive state (anabolic), a negative state (catabolic), or a state of equilibrium. The degree of deviation from the baseline as a result of defined activities can provide a clear indication of the state of approximate nitrogen balance, that is, a balance, or, the level of imbalance. As the user becomes more practiced, the baseline can be confidently adjusted to more accurately reflect the actual state of equilibrium. Fewer tests are subsequently required to detect deviations and determine physical state.

In order that the indicator system be practical for use in athletic training, it must be non-invasive and convenient to perform. The use of a wetable and discardable indicator stick having a reagent thereon that can be passed through a urine stream during normal urination for immediate visual detection and subsequent discard incorporates these features. When coupled with a convenient comparison chart and procedure for determining the user's baseline, the nitrogen balance test kit provides a quantitative means for determining the effect of diet and exercise in a diet, health or fitness program. As additional factors in nutritional health become quantifiable by self-administered urine tests, other reagent zones can be added to the test strip to determine nutritional states, for example vitamin or hormone levels.

DESCRIPTION OF THE PREFERRED EMBODIMENTS

The non-invasive indicator system of this invention is directed at determining the relative level of approximate nitrogen turnover and balance of an individual, particularly an individual engaged in a dietary or exercise program and most specifically in a health and fitness program with attention to both diet and exercise. The indicator system comprises a simple field test method for athletic training programs where both exercise and dietary regimens are deliberately regulated to maximize the positive effect of the training program. The indicator system is designed for human use, but is adaptable to animal use, particularly for training programs involving speed or endurance.

While a number of factors directly influence the nitrogen balance, predominant factors are the quantity and quality of amino acids consumed in the form of dietary protein and the intensity, duration and frequency of the physical training regimen. Intense physical exercise can result in a hypermetabolic state that elevates an individual's energy requirements to three times as high as a basal state. This can result in a catabolic or protein deficient state in which the body responds by utilizing its own amino acid supply resulting in fatigue and muscle cannibalization.

While elaborate quantitative tests can be performed to precisely determine the nitrogen balance of an individual, the procedure requires the exact cataloging of the amino acid intake including the type of protein and its utilization factor, that is, the measure of the effectiveness in which the body can utilize that particular type of protein. Nitrogen loss, through the various pathways previously enumerated, must also be quantified. Intake and loss must then be compared to determine the surplus or deficiency during the period measurements are performed.

This invention provides a personal system for an individual to establish his own baseline level of approximate nitrogen turnover and balance and to determine the state of his nitrogen balance by a simple, non-invasive test.

Figure 1:
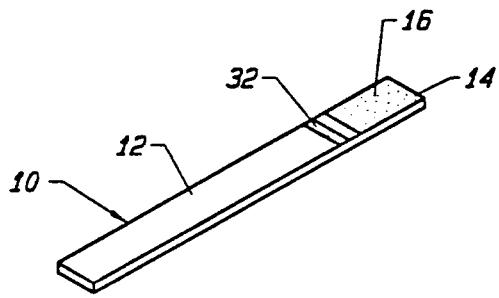
FIG. 1 is a perspective view of a test stick.
Figure 3:
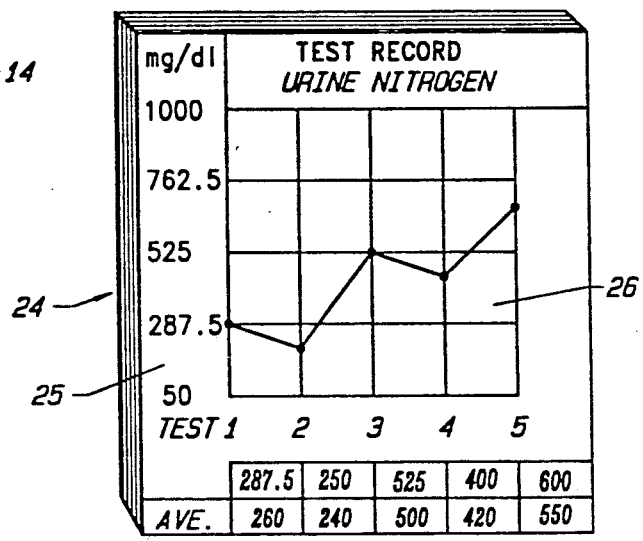
FIG. 3 is a plan view of a test record pad.

As shown in FIG. 1, an indicator stick or detection wand, designated generally by the reference numeral 10 is fabricated from a plastic strip 12 with a reagent area or zone 14 at one end of the strip having a chemical reagent 16 thereon that reacts with urine to indicate the level of nitrogen in the specimen of urine tested. The reactive ingredients of the reagent are urease and bromthymol blue under a permeable membrane. The urease reacts with the urea in the urine to hydrolyze the urea to carbon dioxide and ammonium hydroxide. The liberated ammonium hydroxide increases the pH of the specimen and the shift in alkalinity is indicated by the change in hue of the bromthymol blue. To achieve the range desired, the reagent zone is impregnated with 3.2 I.U. of urease and 33 mcg. bromthymol blue. A non-reactive yellow dye is added to the reagent to provide a convenient color scale change from yellow through green to dark blue-green for comparison with a color block grid.

Figure 2:
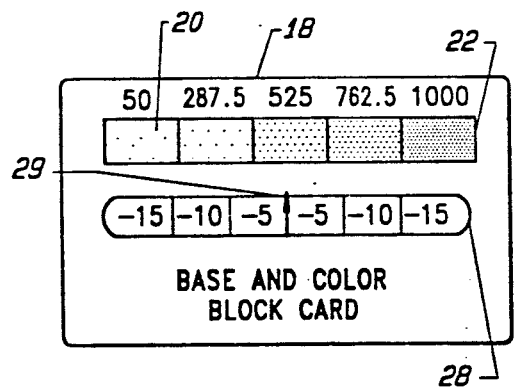
FIG. 2 is a plan view of a color code card.

As shown in FIG. 2 a convenient wallet-size card 18 includes a series of color blocks 20 forming a color block grid 22 having hue variations that are calibrated in range steps of 50, 287.5, 525, 762.5 and 1000 to indicate milligram quantities of urea nitrogen per decaliter of urine sample.

The color block chart is calibrated to define the current level of nitrogen in the urine sample. By careful repetition of a recommended test procedure, a reasonable accuracy can be established in measuring the level of nitrogen in the urine specimen.

In order for the user to have a comparative means to determine whether the tested level of urea nitrogen conforms to an anabolic or catabolic state, the user must establish a baseline representing the balanced state. To establish a personal baseline, the user records a series of tests performed under relatively constant programs of moderate exercise and preferably normal diet. During the period of establishing the baseline, there should be no overall weight gain or weight loss. As an example, to establish a baseline level of approximate nitrogen balance, a period of at least three days is used for testing. The trainee's urine is tested upon waking (within 30 minutes of waking and before breakfast); before lunch; before moderate exercise (zero to 30 minutes prior); after exercise (one to two hours and before eating); and prior to bedtime (zero to 30 minutes).

The same testing procedure is utilized for each test. The indicator stick 10 is wet at the reagent zone by a urine stream or with a least two drops of urine. The reagent zone is wiped clean with a tissue after 15 seconds of contact. At the end of 60 seconds the color of the reagent area is compared with the color blocks 20 of the reference grid 22 on the chart card 18 and the quantitative level of urine nitrogen read.

To conveniently record each result of the tests, a graph pad 24 having sheets 25 with a reference grid 26 for plotting the test results during the baseline test procedure. After three days of testing, a fourth chart can be constructed using the average of each of the five daily periods. This chart will provide a convenient reference to the normal fluctuations that occur during the day.

To convert the nitrogen level tests to a general protein balance baseline, the average five periods are again in turn averaged to provide a single value signifying the baseline balance point for future reference. This can be provided on a stick-on conversion strip 28 as shown in FIG. 2. The stick-on conversion strip has a center balance arrow 29 that aligns with the appropriate nitrogen level in the color block grid 22 representing the averaged value. The conversion strip 28 is divided into plus and minus segments having values designating the approximate excess or deficiency of protein in grams per day.

Figure 4:
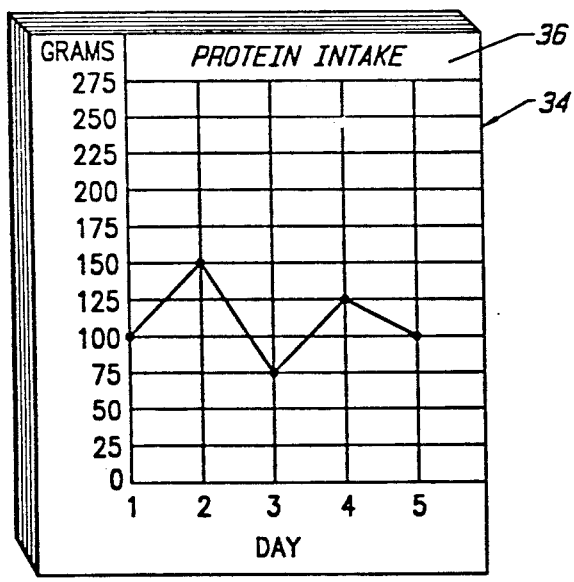
FIG. 4 is a plan view of a diet record pad.

To determine the effects of physical training alterations, the diet should be held relatively constant for five consecutive days while training changes occur. Diet is recorded and listed for nitrogen content on the diet record pad 34 shown in FIG. 4. The diet record pad 34 has sheets 36 with a graph format for recording grams of dietary protein over a five day test period. Fluctuations in nitrogen excretion, relative to nitrogen intake, reflect effects of physical training. Similarly, to determine the effect of dietary alterations, hold the physical training constant for five consecutive days while diet changes take place. Diet is recorded and listed for nitrogen content. Fluctuations in nitrogen excretion, relative to nitrogen intake, reflect effects of the diet. Preferably, for such determinations, the test procedure for determining the baseline, that is the Phase I procedure, should be utilized. In Phase 2, the test procedure can be reduced to three period during the day: waking (within 30 minutes of waking and before breakfast); before an exercise workout (zero to 30 minutes prior); and after the workout (one to two hours and before a snack). If desired, these can similarly be recorded on the record pad 24. Adjustments can be made in the position of the nitrogen balance conversion sticker 28 as more information is compiled. The conversion sticker has a "sticky-back" that permits the strip to be repeatedly repositioned.

Finally, after the trainee has determined a reliably personal baseline, the trainee can engage in a Phase 3 maintenance program where the urine is tested only before workout (zero to 30 minutes prior); and after workout (one to two hours and before a snack).

The use of the system to self-test the urine to determine nitrogen content and establish the trainee's status on an anabolic/catabolic spectrum provides a quantitative basis for modifying the trainee's dietary and workout programs to maximize the utilization of intake protein and minimize the dangers of a catabolic state from excess intense training. The athlete is provided with a means for determining whether his diet is a proper balance of protein and carbohydrates, whether the athlete is wasting intake protein by overconsumption of protein and whether the desired anabolic level is being maintained.

Because of the availability of protein supplements with an accurately determined useable protein content, variations in diet using such supplements can assist in determining a reliable baseline, and can be used to quantitatively adjust protein intake to accommodate variations in the trainee's physical exercise program. Similarly, the availability of other nutritional supplements of quantified content suggest use of a similar urine test strip test to determine excess or deficiency in other nutritional substances detectable in the urine. The auxiliary test utilizes a secondary reagent zone 32 with a reagent that reacts to the nutritional substance or product of the nutritional substance in the urine.

Although the term trainee is used herein, it is to be understood that this term includes animals, as well as humans, and dieters as well as athletes.

While, in the foregoing, embodiments of the present invention have been set forth in considerable detail for the purposes of making a complete disclosure of the invention, it may be apparent to those of skill in the art that numerous changes may be made in such detail without departing from the spirit and principles of the invention.

What is claimed is:

1. A non-invasive nitrogen test kit for determining the approximate nitrogen turnover and balance of a trainee comprising:

a plurality of detection wands each wand having a portion which comprises a reagent area having chemical means that reacts with urine and on reaction with a specimen of the trainee's urine provides a visual indication of the concentration of nitrogen in the urine;

comparative means for gauging the relative nitrogen level in the trainee from test of the specimen of the trainee's urine;

recording means for recording the relative nitrogen level in the trainee's urine from a plurality of tests of specimens of the trainee's urine taken at different times during a controlled regimen for establishing a trainee baseline; and means for comparing nitrogen level during a training regimen with the baseline to determine approximate nitrogen turnover and balance.

2. The non-invasive kit of claim 1 wherein the comparative means includes a color comparison chart with a shading gradient having a plurality of comparative shades, and indicion for gauging the level of nitrogen in the trainee's urine by comparing the reacted reagent area of a urine test wand with the shading gradient for matching the shade of the reacted reagent area with the shade of the gradient and determining the level of nitrogen in the trainee's urine.

3. The non-invasive kit of claim 1 wherein the recording means includes means for averaging the nitrogen level from a plurality of tests to establish an average nitrogen level useable as a baseline.

4. The non-invasive kit of claim 1 wherein the means for comparing nitrogen level during a training regimen with the baseline includes conversion means to establish excess or deficiency in protein.

5. The non-invasive kit of claim 2 wherein the recording means to establish a trainee baseline comprises a use chart having means for recording indicia of nitrogen level from the plurality of tests.

* * * * *